US00PP25519P2

(12) United States Plant Patent
Bean

(10) Patent No.: US PP25,519 P2
(45) Date of Patent: May 5, 2015

(54) ***AGAPANTHUS* PLANT NAMED 'AMBIC001'**

(50) Latin Name: ***Agapanthus* hybrid**
Varietal Denomination: AMBIC001

(71) Applicant: Charles Andrew de Wet, Johannesburg (ZA)

(72) Inventor: Quinton Bean, Johannesburg (ZA)

(73) Assignee: Charles Andrew de Wet, Johannesburg (ZA)

( * ) Notice: Subject to any disclaimer, the term of this patent is extended or adjusted under 35 U.S.C. 154(b) by 85 days.

(21) Appl. No.: 13/998,034

(22) Filed: Sep. 24, 2013

(51) Int. Cl.
*A01H 5/02* (2006.01)

(52) U.S. Cl.
USPC ..... Plt./398

(58) Field of Classification Search
CPC ..... A01H 5/0205; A01H 5/02; A01H 5/00
USPC ..... Plt./398
See application file for complete search history.

*Primary Examiner* — Kent L Bell
(74) *Attorney, Agent, or Firm* — Penny J. Aguirre

(57) ABSTRACT

A new cultivar of *Agapanthus* named 'AMBIC001', that is characterized by its inflorescences that form moderately dense umbels of bicolor flowers that are white with a dark blue base, its semi-deciduous plant habit, its vigorous growth habit with fast sucker production, its long flowering period, and its good cold hardiness.

2 Drawing Sheets

Botanical classification: *Agapanthus* hybrid.
Varietal denomination: 'AMBIC001'.

BACKGROUND OF THE INVENTION

The present invention relates to a new and distinct cultivar of *Agapanthus* of hybrid origin and will be referred to hereafter by its cultivar name, 'AMBIC001'. 'AMBIC001' represents a new perennial herb grown for landscape use.

The new cultivar was derived from a controlled breeding program by the Inventor in Linbro Park, Johannesburg, South Africa. The Inventor made a cross in 2006 between unnamed plants from the Inventors' breeding program. The female and male parents were siblings produced by crossing unnamed plants of *Agapanthus praecox* subsp. *orientalis* and *Agapanthus campanulatus*. The Inventor selected 'AMBIC001' in July of 2008 as a single unique plant amongst the seedlings that resulted from the above cross.

Asexual propagation of the new cultivar was first accomplished by division by the Inventor in Linbro Park, Johannesburg, South Africa in 2009. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'AMBIC001' as a distinct cultivar of *Agapanthus*.

1. 'AMBIC001' exhibits inflorescences that form moderately dense umbels of bicolor flowers that are white with a dark blue base.
2. 'AMBIC001' exhibits a semi-deciduous plant habit.
3. 'AMBIC001' exhibits a long flowering period.
4. 'AMBIC001' exhibits a vigorous growth habit with fast sucker production.
5. 'AMBIC001' exhibits good cold hardiness.

The parent plants of 'AMBIC001', *Agapanthus praecox* subsp. *orientalis*×*Agapanthus campanulatus* hybrids, both differ from 'AMBIC001' in having a slower growth rate, shorter flowering period, and sparser umbels and in being larger in size. 'AMBIC001' can be most closely compared to the cultivars 'Queen Mum' (not patented) and 'Cloudy Days' (not patented). 'Queen Mum' differs from 'AMBIC001' in being much larger in size and in having an evergreen plant habit, a slower growth rate, a slower production rate of suckers and in being less cold hardy. 'Cloudy Days' differs from 'AMBIC001' in being slightly larger in size less cold hardy and in having an evergreen plant habit, a slower growth rate, a slower production rate of suckers.

BRIEF DESCRIPTION OF THE DRAWINGS

The accompanying colored photographs illustrate the overall appearance and distinct characteristics of the new *Agapanthus*. The photographs were taken of 3 month-old plants of 'AMBIC001' as grown (from a rooted tissue culture liner) outdoors in a 9-cm circular container in Oldtown, Republic of Ireland.

The photograph in FIG. 1 provides a view of a plant of 'AMBIC001' in bloom.

Figure 1:
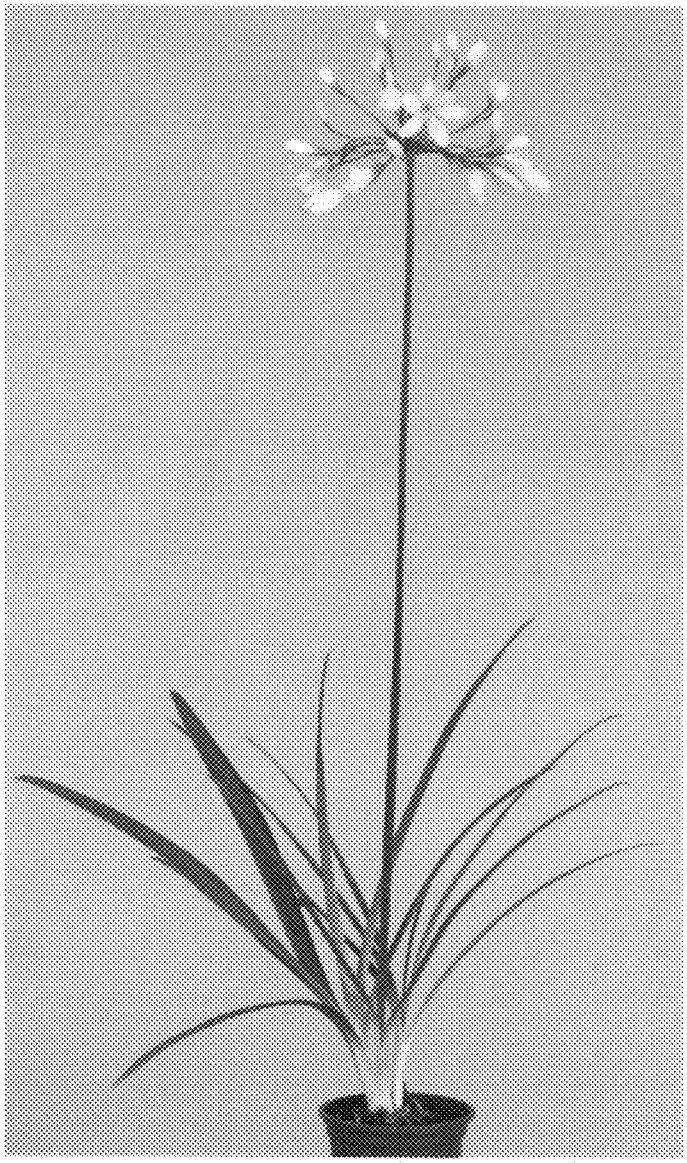
Figure 2:
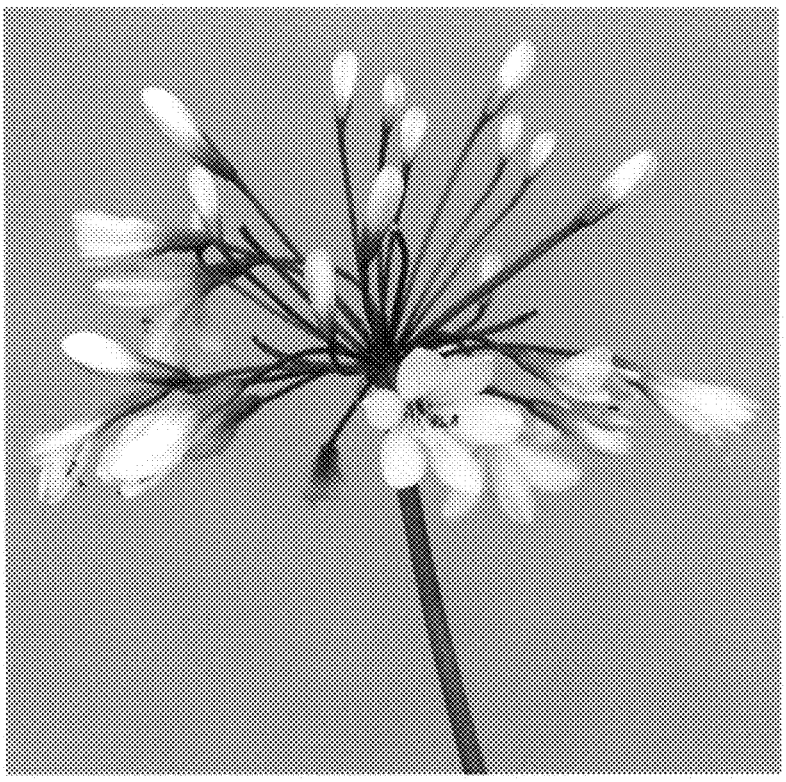

The photograph in FIG. 2 provides a close-up view of an inflorescence of 'AMBIC001'.

Figure 3:
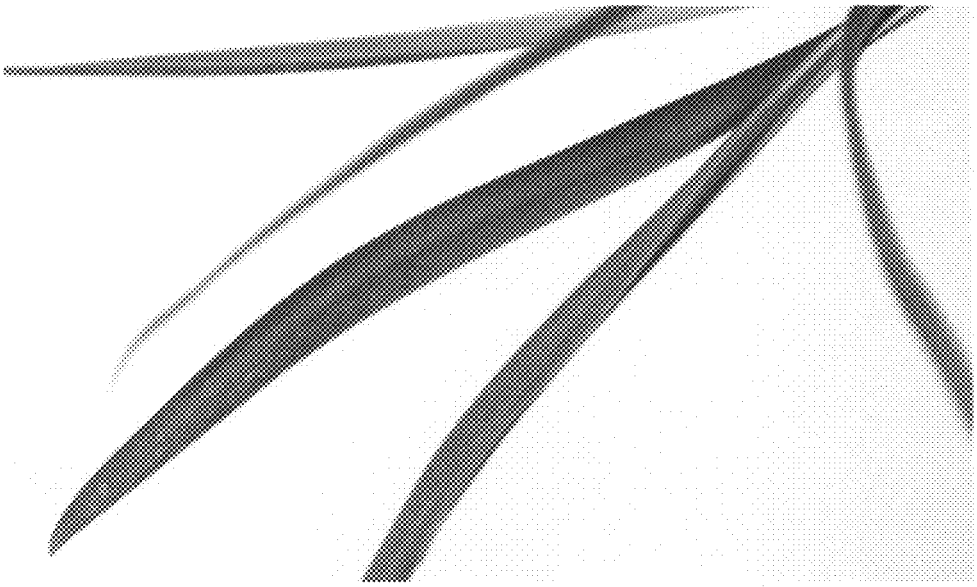

The photograph in FIG. 3 provides a close-up view of the foliage of 'AMBIC001'.

The colors in the photographs are as close as possible with the photographic and printing technology utilized and color values cited in the detailed botanical description accurately describe the colors of the new *Agapanthus*

DETAILED BOTANICAL DESCRIPTION

The general observations and descriptions describe 3 month-old plants of 'AMBIC001' as (from a rooted tissue culture liner) grown in Oldtown, Republic of Ireland. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—Blooms from mid-July to October in South Africa.

*Plant type.*—Herbaceous semi-deciduous herb.

*Plant habit.*—Basal rosettes with inflorescences emerging from the rosette center.

*Height and spread.*—Average of 48.6 in height and 40.0 cm in spread.

*Cold hardiness.*—At least to U.S.D.A. Zone 8.

*Diseases and pests.*—Similar susceptibility and resistance to diseases and pests to other *Agapanthus* varieties.

*Root description.*—Fibrous and fine.

*Propagation.*—Division.

*Growth rate.*—Vigorous (rate dependent on growing conditions) with fast sucker production.

Foliage description:

*Leaf shape.*—Ligulate, very slightly curved.

*Leaf division.*—Simple.

*Leaf base.*—Cuneate.

*Leaf arrangement.*—Distichous.

*Leaf apex.*—Narrow acute.

*Leaf aspect.*—Emerging leaves erect, then cascade.

*Leaf venation.*—Parallel, upper surface; 143A to 144A and lower surface; 144A.

*Leaf margins.*—Entire slightly revolute.

*Leaf size.*—Average of 27.1 cm in length, 1.7 cm in width, and 1 mm in depth.

*Leaf surface.*—Both surfaces smooth, moderately thick and coriaceous with the upper surface moderately glossy and lower surface slightly glossy.

*Leaf number.*—Average of 6 leaves per rosette.

*Leaf color.*—Young leaves, upper surface; 143A, young leaves, lower surface; 144A, mature leaves, upper surface; a blend of 143A and 144A, mature leaves, lower surface; a blend of 137B and 143A.

*Leaf attachment.*—Sessile.

Flower description:

*Inflorescence type.*—Simple umbel.

*Flower fragrance.*—None.

*Flower type.*—Rotate, campanulate, base of tepals fused.

*Flower number.*—Average of 5 flowers per lateral stem.

*Inflorescence size.*—Average of 9 cm in height (excluding peduncle) and 15.4 cm in diameter.

*Flower size.*—An average of 3.2 cm in depth and 3.5 cm in diameter.

*Lastingness of inflorescence.*—Average 7 days.

*Flower aspect.*—Outward.

*Peduncle.*—Strong, rounded, held at an average angle of 0° to 15° (upright=0°), average of 42.6 cm in length and 0.4 cm in width at distal region and 0.6 cm in width at proximal region, color is 143A to 143B.

*Pedicels.*—Very strong, average of 4.4 cm in length and 1.5 mm in width, held erect to outward (0° to 180°), color 146A.

*Flower buds.*—Oblanceolate in shape, average of 2.1 cm in length and 6 mm in width, a blend of 155C and 157D in color with the tip 157B and the base 93C.

*Tepals.*—6 (3 inner and 3 outer), rotate, narrow obovate in shape, lower 45% fused, margins; entire, apex; broadly acute, inner and outer surfaces glabrous, inner and outer tepals an average of 3.5 cm in length, inner tepals 1.0 cm in width, outer tepals 0.8 cm in width, color when opening and fully opened inner surface; NN155C with longitudinal central stripe NN155A and fused base 91C, color when opening and fully opened outer surface; NN155D with longitudinal central stripe NN155B and fused base 92A.

Reproductive organs:

*Gynoecium.*—1 pistil, average of 2.3 cm in length, stigma is narrow clavate in shape and NN155D in color, style is 2.2 cm in length and NN115D in color, ovary is 150B in color.

*Androcoecium.*—6 stamens, anthers are dorsified, oblong in shape, average of 2 mm in length, and 202A in color, filament is 1.8 cm in length and NN155D, base 92C, pollen is moderate in quantity and 7A in color.

*Fruit/seed.*—Have not been observed.

It is claimed:

1. A new and distinct cultivar of *Agapanthus* plant named 'AMBIC001' as herein illustrated and described.

* * * * *